United States Patent
Douglas

(10) Patent No.: US 8,400,169 B2
(45) Date of Patent: Mar. 19, 2013

(54) ACTIVE DISCHARGE OF ELECTRODE

(75) Inventor: Alexander Ulrich Douglas, Goirle (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 690 days.

(21) Appl. No.: 12/599,063

(22) PCT Filed: May 7, 2008

(86) PCT No.: PCT/IB2008/051788
§ 371 (c)(1),
(2), (4) Date: Nov. 6, 2009

(87) PCT Pub. No.: WO2008/135952
PCT Pub. Date: Nov. 13, 2008

(65) Prior Publication Data
US 2010/0219847 A1    Sep. 2, 2010

Related U.S. Application Data

(60) Provisional application No. 60/916,603, filed on May 8, 2007.

(51) Int. Cl.
*G01R 27/26* (2006.01)
(52) U.S. Cl. .................................... 324/686; 324/658
(58) Field of Classification Search .......... 324/658–690; 73/335.04, 780, 862.22, 862.337, 862.339, 73/862.52, 862.626, 514.32, 724
See application file for complete search history.

(56) References Cited

U.S. PATENT DOCUMENTS

| | | | |
|---|---|---|---|
| 3,568,662 A * | 3/1971 | Everett et al. | 600/384 |
| 6,300,616 B1 | 10/2001 | Regensburger | |
| 6,353,324 B1 | 3/2002 | Uber, III et al. | |
| 6,807,438 B1 | 10/2004 | Brun Del Re et al. | |
| 2006/0058694 A1 | 3/2006 | Clark et al. | |

FOREIGN PATENT DOCUMENTS
EP    0570101 A2    11/1993

* cited by examiner

*Primary Examiner* — Jermele M Hollington
*Assistant Examiner* — Alesa Allgood

(57) ABSTRACT

The disclosure is directed to a capacitive sensor for measuring a small biomedical electrical charge originating from an object under test comprising input circuit elements having an electrode for sensing the charge to provide an output signal that is a function of the charge being measured, wherein the electrode has no electrical contact with the object; amplification circuit elements (A) connected to the input circuit elements; processing circuit elements configured for receiving and processing the amplified output signal and to provide the measurement; and conditioning and monitoring circuit elements coupled to at least the input circuit elements comprising monitoring circuit elements and conditioning circuit elements; (R1) wherein the monitoring circuit elements are configured for monitoring the amplified output signal to detect an error in a measurement that is greater than a preset value caused by charge buildup on the electrode; and wherein the conditioning circuit elements are configured to be activated for. discharging the electrode when the error in the measurement is detected by the monitoring circuit elements and the conditioning circuit elements are configured to be deactivated, when the error in the measurement is no longer detected.

13 Claims, 3 Drawing Sheets

ACTIVE DISCHARGE OF ELECTRODE

CROSS REFERENCE TO RELATED APPLICATIONS

This application claims the benefit of U.S. provisional application Ser. No. 60/916,603 filed May 8, 2007, which is incorporated herein by reference.

The disclosure is directed to a capacitive sensor and method of using the same in measuring biomedical signals originating from an object under test, such as measuring the electrocardiogram, electroencephalogram or electromyogram of a human being. The sensor includes monitoring and conditioning circuits for discharging charge buildup on the sensor electrode which can cause errors in measurement.

Measuring biomedical signals is important but not always pleasant for the patient. To measure biomedical signals in an unobtrusive way, capacitive measurement methods are a promising candidate.

Capacitive sensors without direct skin contact provide a larger degree of freedom for the user, resulting in more comfort and unobtrusive measuring and or monitoring of patients.

Such capacitive sensors can be applied to measure a patients electrocardiogram (ECG), electroencephalogram (EEG) or electromyogram (EMG) for example.

Using capacitive sensors also poses the problem of charge build up on the sensing electrode that is coupled to a high impedance/resistance circuitry. This invention disclosure describes a method to actively discharge the electrode and provide a data invalid signal to the rest of the system when discharging takes place to avoid errors in the signal processing.

Current methods of measuring biomedical signals involve the use of electrodes that have to be in contact with the skin. Using this type of measuring technique has the advantage that the measurements obtained are relatively of high quality.

In recent literature, contactless (no galvanic contact) measurements of biomedical signals have been reported [2].

Though the contactless measurements do not offer the stability and accuracy of a contacting measurement, the possibilities of this type of measurements are promising.

Various systems and methodologies have been proposed for measuring charges originating from an object such as U.S. Pat. No. 6,353,324 issued Mar. 5, 2002; U.S. Pat. No. 6,300,616 issued Oct. 9, 2001; and U.S. Pat. No. 6,807,438 issued Oct. 19, 2004; and U.S. Patent Application Number 2006/0058694 published Mar. 16, 2006.

However, problems still persist with these systems and methods, especially when the sensing electrode is used for measuring biomedical charges originating from an object, without contact with the object. The herein disclosed system and methodology overcomes such problems.

The disclosure is directed to a capacitive sensor for measuring a small biomedical electrical charge originating from an object under test comprising input circuit elements having an electrode for sensing the charge to provide an output signal that is a function of the charge being measured, wherein the electrode has no electrical contact with the object; amplification circuit elements connected to the input circuit elements; processing circuit elements configured for receiving and processing the amplified output signal to provide the measurement; and conditioning and monitoring circuit elements coupled to at least the input circuit elements comprising monitoring circuit elements and conditioning circuit elements; wherein the monitoring circuit elements are configured for monitoring the amplified output signal to detect an error in a measurement that is greater than a preset value caused by charge buildup on the electrode; and wherein the conditioning circuit elements are configured to be activated for discharging the electrode when the error in the measurement is detected by the monitoring circuit elements and the conditioning circuit elements are configured to be deactivated when the error in the measurement is no longer detected.

Specifically, it is an object to provide a capacitive sensor for measuring a small biomedical electrical charge originating from an object under test comprising:

input circuit elements configured for sensing the charge to provide an output signal that is a function of the charge being measured, wherein the input circuit elements comprise an electrode for sensing the charge originating from the object and a first resistance element electrically connected to the electrode; wherein the electrode has no electrical contact with the object;

amplification circuit elements connected to the input circuit elements and configured for amplifying the output signal to provide the measurement;

processing circuit elements configured for receiving and processing the amplified output signal and to provide the measurement; and conditioning and monitoring circuit elements coupled to at least the input circuit elements comprising monitoring circuit elements and conditioning circuit elements; wherein the monitoring circuit elements are configured for monitoring the amplified output signal to detect an error in a measurement that is greater than a preset value caused by charge buildup on the electrode; and wherein the conditioning circuit elements are configured to be activated for discharging the electrode when the error in the measurement is detected by the monitoring circuit elements and the conditioning circuit elements are configured to be deactivated when the error in the measurement is no longer detected.

Another object is to provide a sensor wherein the conditioning and monitoring circuit elements further comprise a display indicator for indicating when a measurement is invalid due to the error.

Another object is to provide a sensor wherein the conditioning circuit elements further comprise a second resistance element connected to a switch, the switch being connected to ground potential and configured such that in the closed position the conditioning circuit elements are activated and in the open position the conditioning circuit elements are not activated; wherein the resistance of the second resistance element is much smaller than the resistance of the first resistance element.

Another object is to provide a sensor wherein the switch is an electrical switch, a relay switch or a semiconductor switch.

Another object is to provide a sensor wherein the resistance of the second resistance element and the switch in the closed position is about 0.

Another object is to provide a sensor wherein the resistance of the second resistance element and the switch in the open position is greater than the resistance of the first resistance element.

Another object is to provide a method of measuring a small biomedical electrical charge originating from an object under test comprising:

placing a capacitive sensor in close proximity to, but not in contact with, the surface of the object under test;

measuring the biomedical electrical charge using the capacitive sensor; and transmitting the measurements to a receiving and viewing unit for viewing the measurements;

wherein the capacitive sensor comprises:

input circuit elements configured for sensing the charge to provide an output signal that is a function of the charge being measured, wherein the input circuit elements comprise an electrode for sensing the charge originating from the object and a first resistance element electrically connected to the electrode; wherein the electrode has no electrical contact with the object;

amplification circuit elements connected to the input circuit elements and configured for amplifying the output signal to provide the measurement;

processing circuit elements configured for receiving and processing the amplified output signal and to provide the measurement; and conditioning and monitoring circuit elements coupled to at least the input circuit elements comprising monitoring circuit elements and conditioning circuit elements; wherein the monitoring circuit elements are configured for monitoring the amplified output signal to detect an error in a measurement that is greater than a preset value caused by charge buildup on the electrode; and wherein the conditioning circuit elements are configured to be activated for discharging the electrode when the error in the measurement is detected by the monitoring circuit elements and the conditioning circuit elements are configured to be deactivated when the error in the measurement is no longer detected.

Another object is to provide a method wherein the conditioning and monitoring circuit elements further comprise a display indicator for indicating when a measurement is invalid due to the error.

Another object is to provide a method wherein the conditioning circuit elements further comprise a second resistance element connected to a switch, the switch being connected to ground potential and configured such that in the closed position the conditioning circuit elements are activated and in the open position the conditioning circuit elements are not activated; wherein the resistance of the second resistance element is much smaller than the resistance of the first resistance element.

Another object is to provide a method wherein the switch is an electrical switch, a relay switch or a semiconductor switch.

Another object is to provide a method wherein the resistance of the second resistance element and the switch in the closed position is about 0.

Another object is to provide a method wherein the resistance of the second resistance element and the switch in the open position is greater than the resistance of the first resistance element.

Another object is to provide a method comprising measuring the electrocardiogram, electroencephalogram or electromyogram of a human being.

These and other aspects of the invention are explained in more detail with reference to the following embodiments and with reference to the figures.

FIG. 1 is a conceptual representation showing the basic capacitive probe.

FIG. 2 graphically shows the amplifier output noise as function of input resistance R.

FIG. 3 conceptually depicts an embodiment of a capacitive sensor with active electrode discharging according to the invention.

Figure 1:
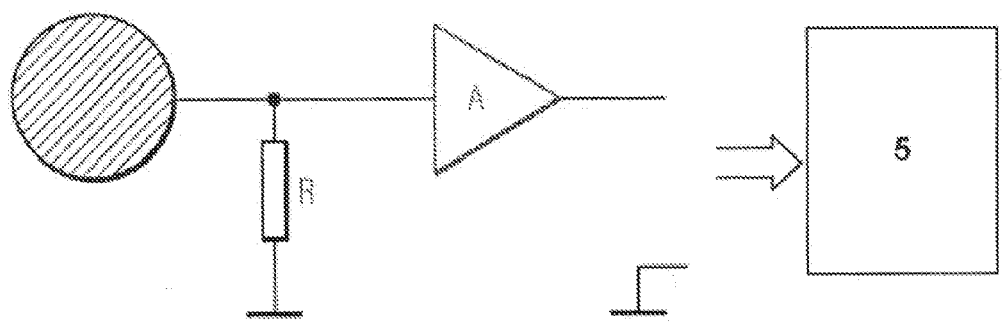
FIG. 1 shows the basic capacitive probe according to the state of the art that can be used, for example, for contactless sensing of electrocardiograms (ECG), electroencephalograms (EEG) and electromyograms (EMG).

The electrode as shown in FIG. 1 does not have to be in galvanic contact with the skin to measure for example ECG, EEG or EMG.

Since the biomedical signals that are measured are very small, the input impedance of a contactless measuring system must be as large as possible. Thus, the value of R as shown in FIG. 1 must be large.

Figure 2:
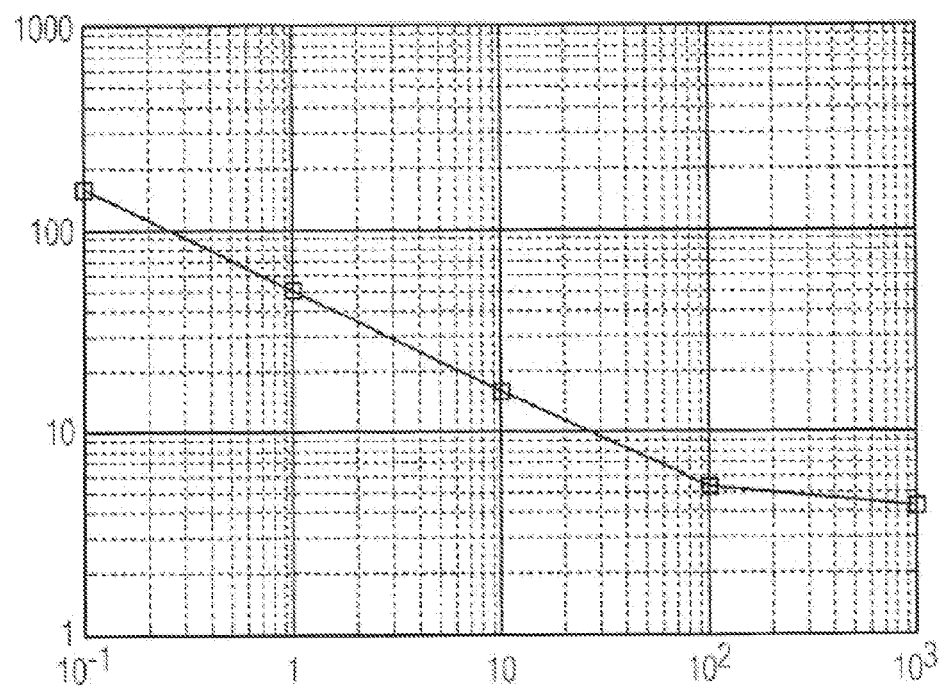

In literature [2], it is also shown that having a large input resistance will result in a lower noise level coming out of the amplifier. The relation between the input resistance R and the amplifier out noise is shown in FIG. 2.

So at least two reasons exist for having a large input impedance/resistance for contactless biomedical sensing systems:

High sensitivity to the small charges generated by the (human) body;

Reducing the output noise of the initial amplifier state of such a sensing system.

Techniques to increase the input impedance/resistance of a contactless biomedical signal sensing system are described in [1].

Due to a large input impedance/resistance of such a sensing system, the system will be very susceptible to interference. Moreover, the electrode of the contactless sensing system can become charged.

The charge of this electrode will be detectable in the output signal of the amplifier. Since the input impedance/resistance of such a sensing system is very high, the charge cannot quickly discharge via the input impedance/resistance, and will result in a long time in which the sensing system is useless.

This invention disclosure proposes to use an addition to the basic capacitive probe that actively discharges the electrode, when the charge accumulated on the electrode interferes with the measuring process.

Figure 3:
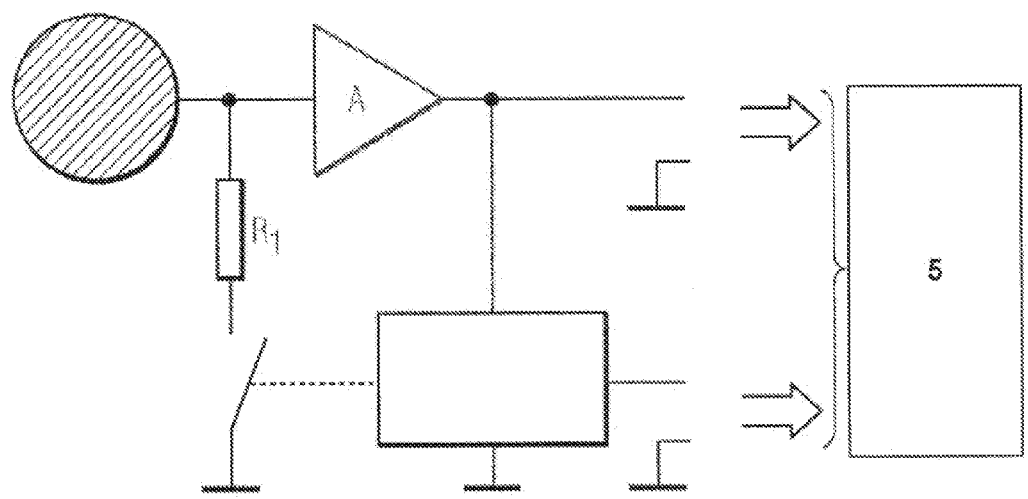

FIG. 3 depicts an embodiment of a capacitive sensor for measuring a small biomedical electrical charge origination from an object under test according to the invention. In this figure, the high input impedance/resistance R (in other words, first resistance element) as shown in FIG. 1 is not shown for convenience.

The active discharging of the electrode is done by a conditioning/monitoring circuit. This circuit monitors the output of the amplifier. If a charge build up on the electrode that interferes with the measurement (further processing) is detected, the electrode is connected to a fixed potential (in this embodiment the ground of the circuitry) via a resistor R1 (in other words, second resistance element). It is contemplated within the scope of the invention that the terms "resistance element" or "resistor" can also refer to circuitry that behaves like an element having resistance. The conditioning/monitoring circuit can monitor the output of the amplifier constantly or intermittently during discrete time periods. The intermittent monitoring is accomplished by adhering to the Nyquist/Shannon criteria, that is, the sampling frequency must be at least twice as high as the signal one samples. For example, when measuring an ECG signal, all relevant information is from the DC-200 Hz level; thus sampling at 1 kHz would be acceptable.

To be able to discharge the electrode very quickly, the relative resistance levels are indicated below according to the invention:

$R_1 \ll R$ $R_{1\ CLOSED\ SWITCH} \approx 0\Omega$.

To not influence the measurement:

$R_{1\ OPEN\ SWITCH} > R$

Note that although the switch is drawn as a real switch, different switch implementations might be possible, for example, utilizing more than one switch or locating one or more switches downstream of the output of the amplifier. Additionally, for example, a relay or a semiconductor implementation of the switch is also contemplated within the scope of the invention. If semiconductor switches are used then R1 might not be chosen to be 0. Doing this could result in electrostatic discharges (ESD) that can potentially destroy the switch. The value of R1 must then be chosen to be in line with the applied switch.

The processing circuit elements 5 are conventional and well known to those skilled in the art and depend on the type of biomedical signal one is measuring. For example an ECG can be measured in the band of DC-200 Hz. For an EMG, the band generally is DC-500 Hz. Also, if one is only interested in the heart rate, and heart rate variability of a patient, DC-100 Hz would be used. So a band filter is almost always applied. Furthermore, the 50 Hz from the main supply (60 Hz in USA and Japan) is the predominant signal. So a notch filter at 50 Hz (or 60 Hz) is often applied. In some cases the higher harmonics of this signal is also large, so notch filters at 100 Hz, 150 Hz, 200 Hz, 250 Hz, 350 Hz (or the higher harmonics of 60 Hz) might be used. There is processing going on behind this filtering. For example, determining the heart rate and heart rate variability requires a different kind of processing than the processing needed to provide a nice looking ECG waveform to a physician. Furthermore, instead of using notch filters, one can also generate the disturbing signal by means of a phase locked loop (PLL), and then subtracting it from the measured signal. Thus, removing the noise can be accomplished in numerous ways. In other words, the charge build up at the sensing electrode is a problem that is overcome by the capacitive sensor and methodology according to the invention herein, regardless of the processing circuit elements 5 utilized for producing a measured signal from the first amplifier that provides a non-usable signal.

Figure 4:
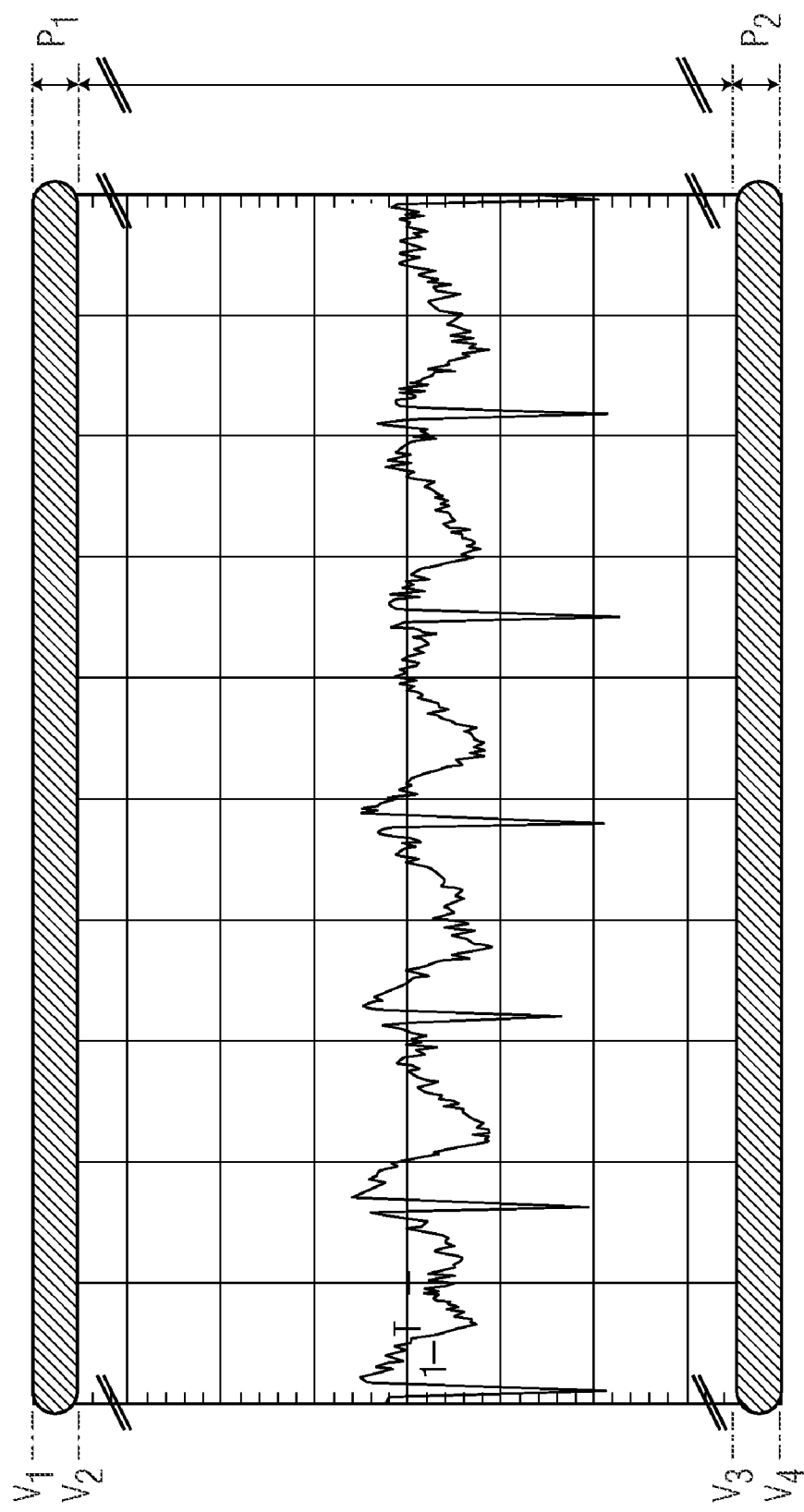
FIG. 4 shows an example of a conditioning/monitoring scheme according to the invention.

An embodiment of a discharging scheme as can be implemented in the conditioning/monitoring circuit is shown in FIG. 4. In this figure a normal situation, ECG is shown. If charge build up occurs on the electrode, the output value of the amplifier will increase. As a result of this, the output of the amplifier could end up between V2 and V1, or between V3 and V4. The values V1 and V4 could, for example, be the output saturation levels of the amplifier. The values V2 and V3 could, for example, be the levels at which the amplifier starts to behave non-linearly. Using these levels, for example, the problem areas of the sensing system can be defined. In FIG. 4, they are called P1 and P2.

A possible discharging scheme would thus be to keep the switch as shown in FIG. 3 open for as long as the amplifier output remains outside the problem areas P1 and P2, the so called safe value Vout (SV) area indicated in FIG. 4. When the amplifier output enters either P1 or P2, then the conditioning/monitoring circuit can close the switch, thereby discharging the electrode, and bringing the amplifier output back into the SV range.

The conditioning/monitoring circuit can generate a discharge indication signal (indicated as "Dis. Ind." in FIG. 3) to let the rest of the system (further processing in FIG. 3) know that the measured signal of the amplifier is invalid.

The approach discussed in this invention disclosure offers a solution for the above mentioned problem.

By discharging the electrode when the charge build up has reached levels that would cause the measurements to be faulty, the charge is removed under control of the conditioning/monitoring circuit, which can also indicate to the rest of the system this momentarily invalidation of the signal.

A second advantage is that when a person that is being measured moves too much, the amplifier output signal can also become invalid (signal in area P1 or P2) because the movement of a person can result in charge movement, which is detected by the capacitive probe. When this happens the conditioning/monitoring circuit also generates a signal that indicates to the rest of the system that the signal is invalid.

While the present invention has been described with respect to specific embodiments thereof, it will be recognized by those of ordinary skill in the art that many modifications, enhancements, and/or changes can be achieved without departing from the spirit and scope of the invention. Therefore, it is manifestly intended that the invention be limited only by the scope of the claims and equivalents thereof.

References

Clark, T. D. and R. J. Prance, C. J. Harland (2006).

ELECTRODYNAMIC SENSORS AND APPLICATIONS THEREOF.

United States Patent Application Publication US 2006/0058694 A1

Prance, R. J. and A. Debray, T. D. Clark, H. Prance, M. Nock, C. J. Harland, A. J. Clippingdale (2000).

AN ULTRA-LOW-NOISE ELECTRICAL-POTENTIAL PROBE FOR HUMAN-BODY SCANNING.

Measurement Science & Technology, Vol. 11, March 2000, Issue 3, p. 291-297.

The invention claimed is:

1. A capacitive sensor for measuring a small biomedical electrical charge originating from an object under test comprising:
    input circuit elements configured for sensing the charge to provide an output signal that is a function of the charge being measured, wherein the input circuit elements comprise an electrode for sensing the charge originating from the object and a first resistance element electrically connected to the electrode; and wherein the electrode has no electrical contact with the object;
    amplification circuit elements connected to the input circuit elements and configured for amplifying the output signal;
    processing circuit elements configured for receiving and processing the amplified output signal and for providing the measurement; and
    conditioning and monitoring circuit elements coupled to at least the input circuit elements comprising monitoring circuit elements and conditioning circuit elements, the conditioning circuit elements comprising a second resistance element connected to a switch;
    wherein the monitoring circuit elements are configured for monitoring the amplified output signal to detect an error in a measurement that is greater than a preset value caused by charge buildup on the electrode, and wherein the conditioning circuit elements are configured to be activated for discharging the electrode when the error in the measurement is detected by the monitoring circuit elements and the conditioning circuit elements are configured to be deactivated when the error in the measurement is no longer detected, and
    wherein the switch is connected to ground potential for discharging the electrode the switch configured such that in the closed position the conditioning circuit elements are activated and in the open position the conditioning elements are not activated.

2. The sensor of claim 1 wherein the conditioning and monitoring circuit elements further comprise a display indicator for indicating when a measurement is invalid due to the error.

3. The sensor of claim 1 wherein the resistance of the second resistance element is much smaller than the resistance of the first resistance element.

4. The sensor of claim 3 wherein the switch is an electrical switch, a relay switch or a semiconductor switch.

5. The sensor of claim 3 wherein the resistance of the second resistance element and the switch in the closed position is about 0.

6. The sensor of claim 3 wherein the resistance of the second resistance element and the switch in the open position is greater than the resistance of the first resistance element.

7. A method of measuring a small biomedical electrical charge originating from an object under test comprising:
    placing a capacitive sensor in close proximity to, but not in contact with, a surface of the object under test;
    measuring the biomedical electrical charge using the capacitive sensor; and
    transmitting the measurements to a receiving and viewing unit for viewing the measurements;
    wherein the capacitive sensor comprises:
        input circuit elements configured for sensing the charge to provide an output signal that is a function of the charge being measured, wherein the input circuit elements comprise an electrode for sensing the charge originating from the object and a first resistance element electrically connected to the electrode; wherein the electrode has no electrical contact with the object;
        amplification circuit elements connected to the input circuit elements and configured for amplifying the output signal for providing the measurement;
        processing circuit elements configured for receiving and processing the amplified output signal and to provide the measurement; and
        conditioning and monitoring circuit elements coupled to at least the input circuit elements comprising monitoring circuit elements and conditioning circuit elements, the conditioning circuit elements comprising a second resistance element connected to a switch;
    wherein the monitoring circuit elements are configured for monitoring the amplified output signal to detect an error in a measurement that is greater than a preset value caused by charge buildup on the electrode, and wherein the conditioning circuit elements are configured to be activated for discharging the electrode when the error in the measurement is detected by the monitoring circuit elements and the conditioning circuit elements are configured to be deactivated when the error in the measurement is no longer detected, and
    wherein the switch is connected to ground potential for discharging the electrode the switch configured such that in the closed position the conditioning circuit elements are activated and in the open position the conditioning elements are not activated.

8. The method of claim 7 wherein the conditioning and monitoring circuit elements further comprise a display indicator for indicating when a measurement is invalid due to the error.

9. The method of claim 7 comprising measuring the electrocardiogram, electroencephalogram or electromyogram of a human being.

10. The method of claim 7 wherein the resistance of the second resistance element is much smaller than the resistance of the first resistance element.

11. The method of claim 10 wherein the switch is an electrical switch, a relay switch or a semiconductor switch.

12. The method of claim 10 wherein the resistance of the second resistance element and the switch in the closed position is about 0.

13. The method of claim 10 wherein the resistance of the second resistance element and the switch in the open position is greater than the resistance of the first resistance element.

* * * * *